US011213226B2

(12) United States Patent
Fennell et al.

(10) Patent No.: US 11,213,226 B2
(45) Date of Patent: Jan. 4, 2022

(54) ANALYTE MONITORING DEVICES AND METHODS

(75) Inventors: Martin J. Fennell, Concord, CA (US); Jean-Pierre Cole, Tracy, CA (US); Theodore John Kunich, Pleasanton, CA (US); Udo Hoss, Castro Valley, CA (US); Benjamin Jay Feldman, Oakland, CA (US); Zenghe Liu, Alameda, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 1220 days.

(21) Appl. No.: 13/267,861

(22) Filed: Oct. 6, 2011

(65) Prior Publication Data
US 2012/0088995 A1 Apr. 12, 2012

Related U.S. Application Data
(60) Provisional application No. 61/391,065, filed on Oct. 7, 2010.

(51) Int. Cl.
*A61B 5/145* (2006.01)
*A61B 5/00* (2006.01)
*A61B 5/1486* (2006.01)
*A61B 5/1473* (2006.01)

(52) U.S. Cl.
CPC ........ *A61B 5/14546* (2013.01); *A61B 5/0004* (2013.01); *A61B 5/14865* (2013.01); *A61B 5/1473* (2013.01); *A61B 5/1486* (2013.01); *A61B 5/14532* (2013.01); *A61B 5/6833* (2013.01); *A61B 2560/0462* (2013.01)

(58) Field of Classification Search
CPC ............ A61B 5/14532; A61B 5/14865; A61B 5/1486; A61B 5/1473; A61B 5/14546; A61B 2560/0462
See application file for complete search history.

(56) References Cited

U.S. PATENT DOCUMENTS

| | | | |
|---|---|---|---|
| 3,581,062 A | 5/1971 | Aston | |
| 3,926,760 A | 12/1975 | Allen et al. | |
| 3,949,388 A | 4/1976 | Fuller | |
| 4,036,749 A | 7/1977 | Anderson | |
| 4,055,175 A | 10/1977 | Clemens et al. | |

(Continued)

FOREIGN PATENT DOCUMENTS

| | | |
|---|---|---|
| CA | 2143172 | 7/2005 |
| CA | 2396613 | 3/2008 |

(Continued)

OTHER PUBLICATIONS

Cheyne, E. H., et al., "Performance of a Continuous Glucose Monitoring System During Controlled Hypoglycaemia in Healthy Volunteers", Diabetes Technology & Therapeutics, vol. 4, No. 5, 2002, pp. 607-613.

(Continued)

Primary Examiner — Christian Jang
Assistant Examiner — Karen E Toth
(74) Attorney, Agent, or Firm — One LLP

(57) ABSTRACT

Methods and devices for providing application specific integrated circuit architecture for a two electrode analyte sensor or a three electrode analyte sensor are provided. Systems and kits employing the same are also provided.

23 Claims, 6 Drawing Sheets

(56) References Cited

U.S. PATENT DOCUMENTS

| | | |
|---|---|---|
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,431,004 A | 2/1984 | Bessman et al. |
| 4,441,968 A | 4/1984 | Emmer et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,165,407 A | 11/1992 | Wilson et al. |
| 5,202,261 A | 4/1993 | Musho et al. |
| 5,210,778 A | 5/1993 | Massart |
| 5,228,449 A | 7/1993 | Christ et al. |
| 5,231,988 A | 8/1993 | Wernicke et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,327,029 A * | 7/1994 | Ericson .................... G06G 7/24 327/350 |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,410,326 A | 4/1995 | Goldstein |
| 5,411,647 A | 5/1995 | Johnson et al. |
| 5,425,868 A | 6/1995 | Pedersen |
| 5,429,602 A | 7/1995 | Hauser |
| 5,431,160 A | 7/1995 | Wilkins |
| 5,431,921 A | 7/1995 | Thombre |
| 5,462,645 A | 10/1995 | Albery et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,532,686 A | 7/1996 | Urbas et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,609,575 A | 3/1997 | Larson et al. |
| 5,628,310 A | 5/1997 | Rao et al. |
| 5,634,468 A | 6/1997 | Platt et al. |
| 5,653,239 A | 8/1997 | Pompei et al. |
| 5,660,163 A | 8/1997 | Schulman et al. |
| 5,665,222 A | 9/1997 | Heller et al. |
| 5,707,502 A | 1/1998 | McCaffrey et al. |
| 5,711,001 A | 1/1998 | Bussan et al. |
| 5,711,861 A * | 1/1998 | Ward .................... C12Q 1/54 204/403.09 |
| 5,724,030 A | 3/1998 | Urbas et al. |
| 5,733,259 A | 3/1998 | Valcke et al. |
| 5,749,907 A | 5/1998 | Mann |
| 5,772,586 A | 6/1998 | Heinonen et al. |
| 5,791,344 A | 8/1998 | Schulman et al. |
| 5,804,047 A | 9/1998 | Karube et al. |
| 5,833,603 A | 11/1998 | Kovacs et al. |
| 5,842,189 A | 11/1998 | Keeler et al. |
| 5,891,049 A | 4/1999 | Cyrus et al. |
| 5,899,855 A | 5/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,980,708 A | 11/1999 | Champagne et al. |
| 5,995,860 A | 11/1999 | Sun et al. |
| 6,001,067 A | 12/1999 | Shults et al. |
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,066,243 A | 5/2000 | Anderson et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,130,623 A | 10/2000 | MacLellan et al. |
| 6,134,461 A | 10/2000 | Say et al. |
| 6,143,164 A | 11/2000 | Heller et al. |
| 6,144,871 A | 11/2000 | Saito et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,248,067 B1 | 6/2001 | Causey, III et al. |
| 6,275,717 B1 | 8/2001 | Gross et al. |

(56) References Cited

U.S. PATENT DOCUMENTS

| | | |
|---|---|---|
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,299,347 B1 | 10/2001 | Pompei |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,359,270 B1 | 3/2002 | Bridson |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,471,689 B1 | 10/2002 | Joseph et al. |
| 6,478,736 B1 | 11/2002 | Mault |
| 6,484,046 B1 | 11/2002 | Say et al. |
| 6,493,069 B1 | 12/2002 | Nagashimada et al. |
| 6,496,729 B2 | 12/2002 | Thompson |
| 6,497,655 B1 | 12/2002 | Linberg et al. |
| 6,498,043 B1 | 12/2002 | Schulman et al. |
| 6,514,718 B2 | 2/2003 | Heller et al. |
| 6,520,326 B2 | 2/2003 | McIvor et al. |
| 6,544,212 B2 | 4/2003 | Galley et al. |
| 6,549,796 B2 | 4/2003 | Sohrab |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,545 B2 | 6/2003 | Knobbe et al. |
| 6,574,510 B2 | 6/2003 | Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,654,625 B1 | 11/2003 | Say et al. |
| 6,656,114 B1 | 12/2003 | Poulsen et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,740,075 B2 | 5/2004 | Lebel et al. |
| 6,740,518 B1 | 5/2004 | Duong et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,789,195 B1 | 9/2004 | Prihoda et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,895,263 B2 | 5/2005 | Shin et al. |
| 6,895,265 B2 | 5/2005 | Silver |
| 6,923,764 B2 | 8/2005 | Aceti et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,983,176 B2 | 1/2006 | Gardner et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,020,508 B2 | 3/2006 | Stivoric et al. |
| 7,022,072 B2 | 4/2006 | Fox et al. |
| 7,024,236 B2 | 4/2006 | Ford et al. |
| 7,024,245 B2 | 4/2006 | Lebel et al. |
| 7,025,425 B2 | 4/2006 | Kovatchev et al. |
| 7,027,848 B2 | 4/2006 | Robinson et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,043,305 B2 | 5/2006 | KenKnight et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,081,195 B2 | 7/2006 | Simpson et al. |
| 7,082,334 B2 | 7/2006 | Boute et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,125,382 B2 | 10/2006 | Zhou et al. |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,171,274 B2 | 1/2007 | Starkweather et al. |
| 7,190,988 B2 | 3/2007 | Say et al. |
| 7,192,450 B2 | 3/2007 | Brauker et al. |

(56) References Cited

U.S. PATENT DOCUMENTS

| | | |
|---|---|---|
| 7,198,606 B2 | 4/2007 | Boecker et al. |
| 7,203,549 B2 | 4/2007 | Schommer et al. |
| 7,207,974 B2 | 4/2007 | Safabash et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,318,816 B2 | 1/2008 | Bobroff et al. |
| 7,324,850 B2 | 1/2008 | Persen et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,347,819 B2 | 5/2008 | Lebel et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Pudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,637,868 B2 | 12/2009 | Saint et al. |
| 7,640,048 B2 | 12/2009 | Dobbies et al. |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,668,596 B2 | 2/2010 | Arx et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,741,734 B2 | 6/2010 | Joannopoulos et al. |
| 7,766,829 B2 | 8/2010 | Sloan et al. |
| 7,768,386 B2 | 8/2010 | Hayter et al. |
| 7,768,387 B2 | 8/2010 | Fennell et al. |
| 7,771,352 B2 | 8/2010 | Shults et al. |
| 7,774,145 B2 | 8/2010 | Brauker et al. |
| 7,778,680 B2 | 8/2010 | Goode et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,813,809 B2 | 10/2010 | Strother et al. |
| 7,826,382 B2 | 11/2010 | Sicurello et al. |
| 7,826,981 B2 | 11/2010 | Goode, Jr. et al. |
| 7,831,310 B2 | 11/2010 | Lebel et al. |
| 7,860,574 B2 | 12/2010 | Arx et al. |
| 7,882,611 B2 | 2/2011 | Shah et al. |
| 7,889,069 B2 | 2/2011 | Fifolt et al. |
| 7,899,511 B2 | 3/2011 | Shults et al. |
| 7,899,545 B2 | 3/2011 | John |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,920,906 B2 | 4/2011 | Goode et al. |
| 7,928,850 B2 | 4/2011 | Hayter et al. |
| 7,955,258 B2 | 6/2011 | Goscha et al. |
| 7,970,448 B2 | 6/2011 | Shults et al. |
| 7,974,672 B2 | 7/2011 | Shults et al. |
| 7,976,466 B2 | 7/2011 | Ward et al. |
| 7,978,063 B2 | 7/2011 | Baldus et al. |
| 7,999,674 B2 | 8/2011 | Kamen |
| 8,010,174 B2 | 8/2011 | Goode et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,150,321 B2 | 4/2012 | Winter et al. |
| 8,150,516 B2 | 4/2012 | Levine et al. |
| 8,179,266 B2 | 5/2012 | Hermle |
| 8,192,394 B2 | 6/2012 | Estes et al. |
| 8,216,138 B1 | 7/2012 | McGarraugh et al. |
| 8,282,549 B2 | 10/2012 | Brauker et al. |
| 2001/0037366 A1 | 11/2001 | Webb et al. |
| 2002/0019022 A1 | 2/2002 | Dunn et al. |
| 2002/0019612 A1 | 2/2002 | Watanabe et al. |
| 2002/0042090 A1 | 4/2002 | Heller et al. |
| 2002/0054320 A1 | 5/2002 | Ogino |
| 2002/0068860 A1 | 6/2002 | Clark |
| 2002/0072784 A1 | 6/2002 | Sheppard et al. |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0161288 A1 | 10/2002 | Shin et al. |
| 2002/0169439 A1 | 11/2002 | Flaherty et al. |
| 2002/0169635 A1 | 11/2002 | Shillingburg |

(56) References Cited

U.S. PATENT DOCUMENTS

| | | |
|---|---|---|
| 2003/0004403 A1 | 1/2003 | Drinan et al. |
| 2003/0010089 A1* | 1/2003 | Holmes .............. G01R 27/2605 73/1.88 |
| 2003/0023317 A1 | 1/2003 | Brauker et al. |
| 2003/0028089 A1 | 2/2003 | Galley et al. |
| 2003/0032874 A1 | 2/2003 | Rhodes et al. |
| 2003/0042137 A1 | 3/2003 | Mao et al. |
| 2003/0055380 A1 | 3/2003 | Flaherty et al. |
| 2003/0060692 A1 | 3/2003 | Ruchti et al. |
| 2003/0065308 A1 | 4/2003 | Lebel et al. |
| 2003/0076082 A1* | 4/2003 | Morgan ................ A61B 5/042 324/71.1 |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0147515 A1 | 8/2003 | Kai et al. |
| 2003/0167035 A1 | 9/2003 | Flaherty et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0225361 A1 | 12/2003 | Sabra |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0041749 A1 | 4/2004 | Dixon |
| 2004/0063435 A1 | 4/2004 | Sakamoto et al. |
| 2004/0064068 A1 | 4/2004 | DeNuzzio et al. |
| 2004/0064088 A1 | 4/2004 | Gorman et al. |
| 2004/0064096 A1 | 4/2004 | Flaherty et al. |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0138588 A1 | 7/2004 | Saikley et al. |
| 2004/0146909 A1 | 7/2004 | Duong et al. |
| 2004/0152622 A1 | 8/2004 | Keith et al. |
| 2004/0153032 A1 | 8/2004 | Garribotto et al. |
| 2004/0158167 A1* | 8/2004 | Smith ................ A61B 5/6843 600/547 |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0219664 A1 | 11/2004 | Heller et al. |
| 2004/0225338 A1 | 11/2004 | Lebel et al. |
| 2004/0236200 A1 | 11/2004 | Say et al. |
| 2004/0254433 A1 | 12/2004 | Bandis et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0070777 A1 | 3/2005 | Cho et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1* | 6/2005 | Simpson et al. ......... 204/403.09 |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0137530 A1 | 6/2005 | Campbell et al. |
| 2005/0143635 A1 | 6/2005 | Kamath et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0239154 A1 | 10/2005 | Feldman et al. |
| 2005/0241957 A1 | 11/2005 | Mao et al. |
| 2005/0244811 A1* | 11/2005 | Soundarrajan ......... B82Y 30/00 435/4 |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0272985 A1 | 12/2005 | Kotulla et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0156796 A1 | 7/2006 | Burke et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |

(56) References Cited

U.S. PATENT DOCUMENTS

| | | |
|---|---|---|
| 2006/0183985 A1 | 8/2006 | Brister et al. |
| 2006/0189863 A1 | 8/2006 | Peyser et al. |
| 2006/0202805 A1 | 9/2006 | Schulman et al. |
| 2006/0211072 A1 | 9/2006 | Ryan et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0229512 A1 | 10/2006 | Petisce et al. |
| 2006/0247508 A1 | 11/2006 | Fennell |
| 2006/0247710 A1 | 11/2006 | Goetz et al. |
| 2006/0253296 A1 | 11/2006 | Liisberg et al. |
| 2006/0258929 A1 | 11/2006 | Goode et al. |
| 2006/0272652 A1 | 12/2006 | Stocker et al. |
| 2006/0281985 A1 | 12/2006 | Ward et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0000163 A1 | 1/2007 | Kamath et al. |
| 2007/0010950 A1 | 1/2007 | Abensour et al. |
| 2007/0000273 A1 | 2/2007 | Stafford |
| 2007/0032706 A1 | 2/2007 | Kamath et al. |
| 2007/0033074 A1 | 2/2007 | Nitzan et al. |
| 2007/0055799 A1 | 3/2007 | Koehler et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0078818 A1 | 4/2007 | Zvitz et al. |
| 2007/0093786 A1 | 4/2007 | Goldsmith et al. |
| 2007/0094216 A1 | 4/2007 | Mathias et al. |
| 2007/0100222 A1 | 5/2007 | Mastrototaro et al. |
| 2007/0106135 A1 | 5/2007 | Sloan et al. |
| 2007/0118405 A1 | 5/2007 | Campbell et al. |
| 2007/0124002 A1 | 5/2007 | Estes et al. |
| 2007/0149875 A1 | 6/2007 | Quyang et al. |
| 2007/0151869 A1 | 7/2007 | Heller et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0208246 A1 | 9/2007 | Brauker et al. |
| 2007/0213657 A1 | 9/2007 | Jennewine et al. |
| 2007/0002443 A1 | 10/2007 | Talbot et al. |
| 2007/0228071 A1 | 10/2007 | Kamen et al. |
| 2007/0232880 A1 | 10/2007 | Siddiqui et al. |
| 2007/0235331 A1 | 10/2007 | Simpson et al. |
| 2007/0249922 A1 | 10/2007 | Peyser et al. |
| 2007/0253021 A1 | 11/2007 | Mehta et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0271285 A1 | 11/2007 | Eichorn et al. |
| 2007/0282299 A1 | 12/2007 | Hellwig |
| 2007/0285238 A1 | 12/2007 | Batra |
| 2007/0299617 A1 | 12/2007 | Willis |
| 2008/0009692 A1 | 1/2008 | Stafford |
| 2008/0017522 A1 | 1/2008 | Heller et al. |
| 2008/0018433 A1 | 1/2008 | Pitt-Pladdy |
| 2008/0021436 A1 | 1/2008 | Wolpert et al. |
| 2008/0021666 A1 | 1/2008 | Goode, Jr. et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0064943 A1 | 3/2008 | Talbot et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0108942 A1 | 5/2008 | Brister et al. |
| 2008/0119705 A1 | 5/2008 | Patel et al. |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0161707 A1* | 7/2008 | Farringdon ......... A61B 5/0428 600/509 |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0182537 A1 | 7/2008 | Manku et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208026 A1 | 8/2008 | Noujaim et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0235469 A1 | 9/2008 | Drew |
| 2008/0242961 A1 | 10/2008 | Brister et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262304 A1* | 10/2008 | Nisani ................ A61B 1/00016 600/118 |
| 2008/0262469 A1 | 10/2008 | Brister et al. |
| 2008/0269723 A1 | 10/2008 | Mastrototaro et al. |
| 2008/0275313 A1 | 11/2008 | Brister et al. |
| 2008/0281179 A1* | 11/2008 | Fennell ............... A61B 5/14532 600/347 |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |

(56) References Cited

U.S. PATENT DOCUMENTS

| | | |
|---|---|---|
| 2008/0288204 A1 | 11/2008 | Hayter et al. |
| 2008/0296155 A1 | 12/2008 | Shults et al. |
| 2008/0306368 A1 | 12/2008 | Goode et al. |
| 2008/0306434 A1 | 12/2008 | Dobbies et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319279 A1 | 12/2008 | Ramsay et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006133 A1 | 1/2009 | Weinert et al. |
| 2009/0012379 A1 | 1/2009 | Goode et al. |
| 2009/0018424 A1 | 1/2009 | Kamath et al. |
| 2009/0018425 A1 | 1/2009 | Quyang et al. |
| 2009/0027040 A1* | 1/2009 | Kermani ............ G01N 27/3273 324/123 R |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054748 A1 | 2/2009 | Feldman et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105636 A1 | 4/2009 | Hayter et al. |
| 2009/0112478 A1 | 4/2009 | Mueller, Jr. et al. |
| 2009/0118604 A1* | 5/2009 | Phan ................ A61B 5/14532 600/345 |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0001923 A1 | 7/2009 | Shariati et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0209904 A1* | 8/2009 | Peeters ................ A61B 5/0002 604/66 |
| 2009/0216100 A1 | 8/2009 | Ebner et al. |
| 2009/0216103 A1 | 8/2009 | Brister et al. |
| 2009/0227855 A1 | 9/2009 | Hill et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0240440 A1 | 9/2009 | Shurabura et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0253973 A1 | 10/2009 | Bashan et al. |
| 2009/0259118 A1 | 10/2009 | Feldman et al. |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0292188 A1 | 11/2009 | Hoss et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2009/0318792 A1 | 12/2009 | Fennell et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0056992 A1 | 3/2010 | Hayter et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbies et al. |
| 2010/0081909 A1 | 4/2010 | Budiman et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121169 A1 | 5/2010 | Petisce et al. |

(56) References Cited

U.S. PATENT DOCUMENTS

| | | | |
|---|---|---|---|
| 2010/0152554 A1 | 6/2010 | Steine et al. | |
| 2010/0160759 A1 | 6/2010 | Celentano et al. | |
| 2010/0168538 A1 | 7/2010 | Keenan et al. | |
| 2010/0168546 A1 | 7/2010 | Kamath et al. | |
| 2010/0190435 A1 | 7/2010 | Cook et al. | |
| 2010/0191082 A1 | 7/2010 | Brister et al. | |
| 2010/0191085 A1 | 7/2010 | Budiman | |
| 2010/0191472 A1 | 7/2010 | Doniger et al. | |
| 2010/0198034 A1 | 8/2010 | Thomas et al. | |
| 2010/0198142 A1 | 8/2010 | Sloan et al. | |
| 2010/0234710 A1 | 9/2010 | Budiman et al. | |
| 2010/0240975 A1 | 9/2010 | Goode et al. | |
| 2010/0274515 A1 | 10/2010 | Hoss et al. | |
| 2010/0277342 A1* | 11/2010 | Sicurello | A61B 5/7203 340/870.3 |
| 2010/0312176 A1 | 12/2010 | Hans-Martin et al. | |
| 2010/0317958 A1* | 12/2010 | Beck | A61B 5/0006 600/391 |
| 2011/0004276 A1 | 1/2011 | Blair et al. | |
| 2011/0024043 A1 | 2/2011 | Boock et al. | |
| 2011/0024307 A1 | 2/2011 | Simpson et al. | |
| 2011/0027127 A1 | 2/2011 | Simpson et al. | |
| 2011/0027453 A1 | 2/2011 | Boock et al. | |
| 2011/0027458 A1 | 2/2011 | Boock et al. | |
| 2011/0028815 A1 | 2/2011 | Simpson et al. | |
| 2011/0028816 A1 | 2/2011 | Simpson et al. | |
| 2011/0077490 A1 | 3/2011 | Simpson et al. | |
| 2011/0148905 A1 | 6/2011 | Simmons et al. | |
| 2011/0152637 A1 | 6/2011 | Kateraas et al. | |
| 2011/0213225 A1* | 9/2011 | Bernstein | G06Q 50/22 600/309 |
| 2011/0257495 A1* | 10/2011 | Hoss | A61B 5/14532 600/347 |
| 2011/0257895 A1 | 10/2011 | Brauker et al. | |
| 2011/0320130 A1 | 12/2011 | Valdes et al. | |
| 2011/0320167 A1 | 12/2011 | Budiman | |
| 2012/0078071 A1 | 3/2012 | Bohm et al. | |
| 2012/0108934 A1 | 5/2012 | Valdes et al. | |
| 2012/0161793 A1* | 6/2012 | Satake | B60N 2/002 324/658 |
| 2012/0173200 A1 | 7/2012 | Breton et al. | |

FOREIGN PATENT DOCUMENTS

| | | | |
|---|---|---|---|
| CA | 2413148 | | 8/2010 |
| DE | 4401400 | | 7/1995 |
| EP | 0098592 | | 1/1984 |
| EP | 0127958 | | 12/1984 |
| EP | 0320109 | | 6/1989 |
| EP | 0353328 | | 2/1990 |
| EP | 0390390 | | 10/1990 |
| EP | 0396788 | | 11/1990 |
| EP | 0286118 | | 1/1995 |
| EP | 0724859 | | 8/1996 |
| EP | 0678308 | | 5/2000 |
| EP | 1048264 | | 11/2000 |
| EP | 1292218 | | 3/2003 |
| EP | 1077634 | | 7/2003 |
| EP | 1568309 | | 8/2005 |
| EP | 1666091 | | 6/2006 |
| EP | 1703697 | | 9/2006 |
| EP | 1704893 | | 9/2006 |
| EP | 1897487 | | 11/2009 |
| EP | 1897492 | | 11/2009 |
| EP | 2113864 | | 11/2009 |
| EP | 1897488 | | 12/2009 |
| EP | 1681992 | | 4/2010 |
| EP | 1448489 | | 8/2010 |
| EP | 1971396 | | 8/2010 |
| EP | 2201969 | | 3/2011 |
| EP | 2153382 | | 2/2012 |
| EP | 2284773 | | 2/2012 |
| JP | 5353991 B2 * | 11/2013 | B60N 2/002 |
| WO | WO-1993/006237 | | 4/1993 |
| WO | WO-1996/025089 | | 8/1996 |
| WO | WO-1996/035370 | | 11/1996 |
| WO | WO-1997/033513 | | 9/1997 |
| WO | WO-1998/035053 | | 8/1998 |
| WO | WO-1999/056613 | | 11/1999 |
| WO | WO-2000/049940 | | 8/2000 |
| WO | WO-2000/059370 | | 10/2000 |
| WO | WO-2000/074753 | | 12/2000 |
| WO | WO-2000/078992 | | 12/2000 |
| WO | WO-2001/052935 | | 7/2001 |
| WO | WO-2001/054753 | | 8/2001 |
| WO | WO-2002/016905 | | 2/2002 |
| WO | WO-2002/058537 | | 8/2002 |
| WO | WO-2003/076893 | | 9/2003 |
| WO | WO-2003/082091 | | 10/2003 |
| WO | WO-2003/085372 | | 10/2003 |
| WO | WO-2004/047445 | | 6/2004 |
| WO | WO-2004/061420 | | 7/2004 |
| WO | WO-2005/040404 | | 5/2005 |
| WO | WO-2005/041766 | | 5/2005 |
| WO | WO-2005/045744 | | 5/2005 |
| WO | WO-2005/089103 | | 9/2005 |
| WO | WO-2006/024671 | | 3/2006 |
| WO | WO-2006/032653 | | 3/2006 |
| WO | WO-2006/051466 | | 5/2006 |
| WO | WO-2006/064397 | | 6/2006 |
| WO | WO-2006/079114 | | 7/2006 |
| WO | WO-2006/118947 | | 11/2006 |
| WO | WO-2006/124099 | | 11/2006 |
| WO | WO-2007/007459 | | 1/2007 |
| WO | WO-2008/086541 | | 7/2008 |
| WO | WO-2009/086216 | | 7/2009 |
| WO | WO-2010/077329 | | 7/2010 |
| WO | WO-2011/022418 | | 2/2011 |

OTHER PUBLICATIONS

Kuure-Kinsey, M., et al., "A Dual-Rate Kalman Filter for Continuous Glucose Monitoring", *Proceedings of the 28th IEEE, EMBS Annual International Conference, New York City*, 2006, pp. 63-66.

Lo, B., et al., "Key Technical Challenges and Current Implementations of Body Sensor Networks", *Body Sensor Networks*, 2005, pp. 1-5.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.

Parker, R., et al., "Robust H∞ Glucose Control in Diabetes Using a Physiological Model", *AIChE Journal*, vol. 46, No. 12, 2000, pp. 2537-2549.

Rodriguez, N., et al., "Flexible Communication and Control Protocol for Injectable Neuromuscular Interfaces", *IEEE Transactions on Biomedical Circuits and Systems*, vol. 1, No. 1, 2007, pp. 19-27.

PCT Application No. PCT/US2011/055177, International Preliminary Report on Patentability and Written Opinion of the International Searching Authority dated Apr. 18, 2013.

Mougiakakou, et al., "A Real Time Simulation Model of Glucose-Insulin Metabolism for Type 1 Diabetes Patients", *Proceedings of the 2005 IEEE*, 2005, pp. 298-301.

PCT Application No. PCT/US2011/055177, International Search Report and Written Opinion of the International Searching Authority dated Feb. 23, 2012.

Armour, J. C., et al., "Application of Chronic Intravascular Blood Glucose Sensor in Dogs", *Diabetes*, vol. 39, 1990, pp. 1519-1526.

Aussedat, B., et al., "A User-Friendly Method for Calibrating a Subcutaneous Glucose Sensor-Based Hypoglycaemic Alarm", *Biosensors & Bioelectronics*, vol. 12, No. 11, 1997, pp. 1061-1070.

Bennion, N., et al., "Alternate Site Glucose Testing: A Crossover Design", *Diabetes Technology & Therapeutics*, vol. 4, No. 1. 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

(56) References Cited

OTHER PUBLICATIONS

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technology*, vol. 1, No. 2, 2007, pp. 181-192.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Garg, S., et al., "Improvement in Glycemic Excusions with a Transcutaneous, Real-Time Continuous Glucose Sensor", *Diabetes Care*, vol. 29. No. 1, 2006, pp. 44-50.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, p. 198.

Jungheim, K., et al., "How Rapid Does Glucose Concentration Change in Daily Life of Patients with Type 1 Diabetes?", 2002, p. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain The Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectoscopy", *Clinical Chemistry*, vol. 45, No. 9. 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29. No. 13, 1996, pp. 2289-2308.

Schmtdtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

EP, 11831644.7 Extended Search Report, dated Apr. 17, 2018.

* cited by examiner

ANALYTE MONITORING DEVICES AND METHODS

RELATED APPLICATION

The present application claims the benefit of U.S. provisional application No. 61/391,065 filed Oct. 7, 2010, entitled "Analyte Monitoring Devices and Methods", the disclosure of which is incorporated herein by reference for all purposes.

BACKGROUND

The detection and/or monitoring of glucose levels or other analytes, such as lactate, oxygen, A1C, or the like, in certain individuals is vitally important to their health. For example, the monitoring of glucose is particularly important to individuals with diabetes. Diabetics generally monitor glucose levels to determine if their glucose levels are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with diabetic condition do not monitor their glucose levels as frequently as they should due to a combination of factors including convenience, testing discretion, pain associated with glucose testing, and/or cost.

Devices have been developed for the automatic or continuous monitoring of analyte(s), such as glucose, in bodily fluid such as in the blood stream or in interstitial fluid ("ISF"), or other biological fluid. Some of these analyte measuring devices are configured so that at least a portion of the devices are positioned below a skin surface of a user, e.g., in a blood vessel or in the subcutaneous tissue of a user, so that the monitoring is accomplished in vivo.

With the continued development of analyte monitoring devices and systems, there is a need for such analyte monitoring devices, systems, and methods, as well as for processes for manufacturing analyte monitoring devices and systems that are cost effective, convenient, and with reduced pain, provide discreet monitoring to encourage frequent analyte monitoring to improve glycemic control.

INCORPORATION BY REFERENCE

Patents, applications and/or publications described herein, including the following patents, applications and/or publications are incorporated herein by reference for all purposes: U.S. Pat. Nos. 4,545,382, 4,711,245, 5,262,035, 5,262,305, 5,264,104, 5,320,715, 5,356,786, 5,509,410, 5,543,326, 5,593,852, 5,601,435, 5,628,890, 5,820,551, 5,822,715, 5,899,855, 5,918,603, 6,071,391, 6,103,033, 6,120,676, 6,121,009, 6,134,461, 6,143,164, 6,144,837, 6,161,095, 6,175,752, 6,270,455, 6,284,478, 6,299,757, 6,338,790, 6,377,894, 6,461,496, 6,503,381, 6,514,460, 6,514,718, 6,540,891, 6,560,471, 6,579,690, 6,591,125, 6,592,745, 6,600,997, 6,605,200, 6,605,201, 6,616,819, 6,618,934, 6,650,471, 6,654,625, 6,676,816, 6,730,200, 6,736,957, 6,746,582, 6,749,740, 6,764,581, 6,773,671, 6,881,551, 6,893,545, 6,932,892, 6,932,894, 6,942,518, 7,041,468, 7,167,818, 7,299,082, and 7,866,026, U.S. Patent Publication Nos. 2004/0186365, 2005/0182306, 2006/0025662, 2006/0091006, 2007/0056858, 2007/0068807, 2007/0095661, 2007/0108048, 2007/0199818, 2007/0227911, 2007/0233013, 2008/0066305, 2008/0081977, 2008/0102441, 2008/0148873, 2008/0161666, 2008/0267823, 2009/0054748, 2009/0294277, 2010/0213057, 2010/0081909, 2009/0247857, 2011/0106126, 2011/0082484, 2010/0326842, 2010/0198034, 2010/0324392, 2010/0230285, 2010/0313105, 2011/0213225, 2011/0021889, 2011/0193704, 2011/0190603, and 2011/0191044, U.S. patent application Ser. Nos. 13/071,461, 13/071,487, and 13/071,497, and U.S. Provisional Application No. 61/325,260.

SUMMARY

In view of the foregoing, devices, methods and systems for providing electronics for coupling to analyte sensors are provided including, for example, application specific integrated circuit (ASIC) configurations that provide electrical coupling of electrodes of analyte sensors having one or more configurations such as, for example, self powered two electrode analyte sensors, or three electrode analyte sensors.

Embodiments of the present disclosure include analyte monitoring devices. Certain aspects of analyte monitoring devices comprise an analyte sensor including a plurality of electrodes, including an in vivo portion of the analyte sensor configured for fluid contact with a bodily fluid under a skin layer, the analyte sensor configured to monitor an analyte level in the bodily fluid and to generate one or more signals associated with the monitored analyte level and sensor electronics including a sensor interface section and a data processing section, the sensor interface section configured to electrically couple to the plurality of electrodes of the analyte sensor, and the data processing section configured to process one or more signals received from the analyte sensor, wherein the sensor interface section includes an electrical interface to couple to two electrodes of the plurality of electrodes, or three electrodes of the plurality of electrodes, and further wherein the data processing section includes an application specific integrated circuit with programmable logic to perform one or more operations of the data processing section including processing the one or more signals from the analyte sensor for filtering, calibration, storage, transmission, or one or more combinations thereof.

Certain embodiments include providing an analyte sensor including a plurality of electrodes, including an in vivo portion of the analyte sensor for fluid contact with a bodily fluid under a skin layer, the analyte sensor for monitoring an analyte level in the bodily fluid and for generating one or more signals associated with the monitored analyte level and providing sensor electronics including a sensor interface section and a data processing section, wherein providing sensor electronics includes configuring the sensor interface section to electrically couple to the plurality of electrodes of the analyte sensor, and configuring the data processing section to process one or more signals received from the analyte sensor, wherein configuring the sensor interface section includes providing an electrical interface to couple to two electrodes of the plurality of electrodes, or three electrodes of the plurality of electrodes and further wherein configuring the data processing section includes providing an application specific integrated circuit with programmable logic to perform one or more operations of the data processing section including processing the one or more signals from the analyte sensor for filtering, calibration, storage, transmission, or one or more combinations thereof.

These and other objects, features and advantages of the present disclosure will become more fully apparent from the following detailed description of the embodiments, the appended claims and the accompanying drawings.

DETAILED DESCRIPTION

Before the present disclosure is described in detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Figure 1:
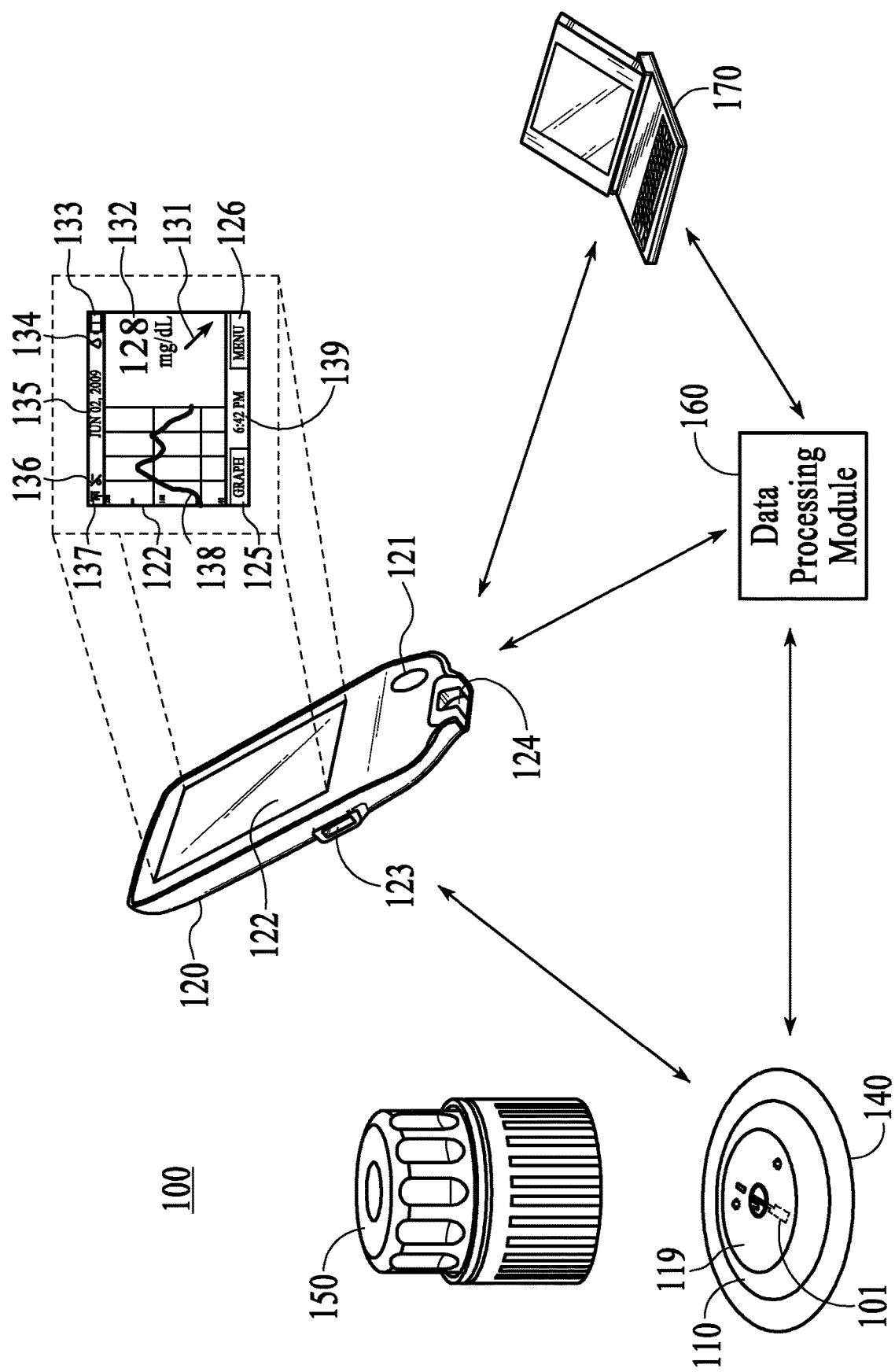
FIG. 1 shows an overall in vivo sensor based analyte monitoring system for use in certain embodiments of the present disclosure.

FIG. 1 shows an exemplary in vivo based analyte monitoring system 100 in accordance with embodiments of the present disclosure. As shown, in certain embodiments, analyte monitoring system 100 includes on body electronics 110 electrically coupled to in vivo analyte sensor 101 (a proximal portion of which is shown in FIG. 1) and attached to adhesive layer 140 for attachment on a skin surface on the body of a user. On body electronics 110 includes on body housing 119, that defines an interior compartment. Also shown in FIG. 1 is insertion device 150 that, when operated, transcutaneously positions a portion of analyte sensor 101 through a skin surface and in fluid contact with ISF, and positions on body electronics 110 and adhesive layer 140 on a skin surface. In certain embodiments, on body electronics 110, analyte sensor 101 and adhesive layer 140 are sealed within the housing of insertion device 150 before use, and in certain embodiments, adhesive layer 140 is also sealed within the housing or itself provides a terminal seal of the insertion device 150. Devices, systems and methods that may be used with embodiments herein are described, e.g., in U.S. Patent Publication Nos. 2010/0198034, 2010/0324392 and 2011/0213225, the disclosures of each of which are incorporated herein by reference for all purposes.

Referring back to the FIG. 1, analyte monitoring system 100 includes display device 120 which includes a display 122 to output information to the user, an input component 121 such as a button, actuator, a touch sensitive switch, a capacitive switch, pressure sensitive switch, jog wheel or the like, to input data or command to display device 120 or otherwise control the operation of display device 120.

In certain embodiments, input component 121 of display device 120 may include a microphone and display device 120 may include software configured to analyze audio input received from the microphone, such that functions and operation of the display device 120 may be controlled by voice commands. Display device 120 also includes data communication port 123 for wired data communication with external devices such as remote terminal (personal computer) 170, for example. Display device 120 may also include an integrated in vitro glucose meter, including in vitro test strip port 124 to receive an in vitro glucose test strip for performing in vitro blood glucose measurements.

Referring still to FIG. 1, display 122 in certain embodiments is configured to display a variety of information—some or all of which may be displayed at the same or different time on display 122. Display 122 may include but is not limited to graphical display 138, numerical display 132, trend or directional arrow display 131, date display 135, time of day information display 139, battery level indicator display 133, sensor calibration status icon display 134, and wireless connectivity status icon display 137 that provides indication of wireless communication connection with other devices such as on body electronics, data processing module 160, and/or remote terminal 170. As additionally shown in FIG. 1, display 122 may further include simulated touch screen button 125, 126 for accessing menus, changing display graph output configurations or otherwise for controlling the operation of display device 120.

Further details and other display embodiments can be found in, e.g., U.S. Patent Publication Nos. 2011/0193704 and 2011/0213225, the disclosures of each of which are incorporated herein by reference for all purposes.

After the positioning of on body electronics 110 on the skin surface and analyte sensor 101 in vivo to establish fluid contact with ISF (or other appropriate body fluid), on body electronics 110 in certain embodiments is configured to wirelessly communicate analyte related data (such as, for example, data corresponding to monitored analyte level and/or monitored temperature data, and/or stored historical analyte related data) when on body electronics 110 receives a command or request signal from display device 120. In certain embodiments, data from on body electronics 110 is retrieved using display device 120 or a reader via a wireless link that operates using a near field reflective communication technique such as used in radio frequency identification (RFID) system. Using such systems, in certain embodiments, analyte measurement from analyte sensor 101 can be obtained by positioning the display device 120 within a short range of the on body electronics 110, and optionally actuating a button such as input component 121.

In certain embodiments, the RFID communication operates at a nominal operating frequency of 13.56 MHz, with minimum antenna input voltage for normal operation at about 2.5 Volts. Data rate for transmit and receive between on body electronics 110 and display device 120 may be about 20-30 kbits/second, or about 22-28 kbits/second, or about 26.48 kbits/second (data bits) in certain embodiments. Within the scope of the present disclosure, other operating frequencies for RFID communication as well as other parameters such as data transmission rates, and/or antenna input voltages are contemplated.

In certain embodiments, on body electronics 110 may be configured to at least periodically broadcast real time data associated with monitored analyte level which is received by display device 120 when display device 120 is within communication range of the data broadcast from on body electronics 110, i.e., it does not need a command or request from a display device to send information.

In certain embodiments, the received data from the on body electronics 110 may be stored (permanently or temporarily) in one or more memory of the display device 120. Referring still to FIG. 1, also shown in analyte monitoring system 100 are data processing module 160 and remote terminal 170. Remote terminal 170 may include a personal computer, a server terminal a laptop computer or other suitable data processing devices including software for data management and analysis and communication with the components in the analyte monitoring system 100.

Data processing module 160 may include components to communicate using one or more wireless communication protocols such as, for example, but not limited to, infrared (IR) protocol, BLUETOOTH® protocol, ZIGBEE® protocol, and 802.11 wireless LAN protocol. Additional description of communication protocols including those based on BLUETOOTH® protocol and/or ZIGBEE® protocol can be found in U.S. Patent Publication No. 2006/0193375 incorporated herein by reference for all purposes.

In a further aspect, software algorithms for execution by data processing module 160 may be provided to a communication device such as a mobile telephone including, for example, WiFi or Internet enabled smart phones or personal digital assistants (PDAs) as a downloadable application for execution by the downloading communication device. Additional details describing field upgradability of software of portable electronic devices, and data processing are provided in U.S. Patent Publication Nos. 2010/0198034, 2010/0313105, 2010/0198142, 2010/0204557 and 2011/0126188, and U.S. Provisional Application No. 61/325,155 the disclosures of each of which are incorporated by reference herein for all purposes.

Figure 2:
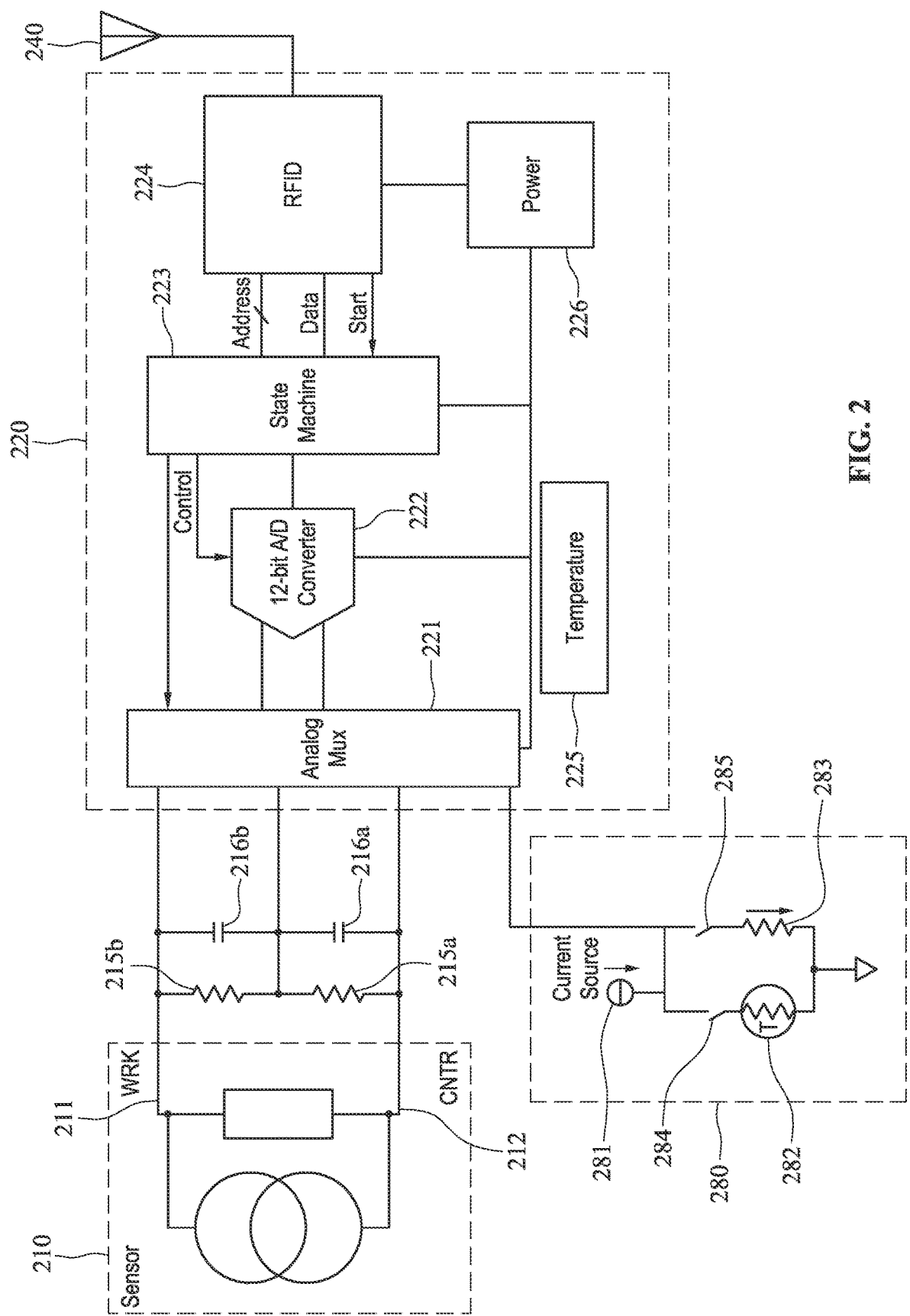
FIG. 2 illustrates a block diagram of the on body electronics configured for operation with a two electrode analyte sensor in certain embodiments.

FIG. 2 illustrates a block diagram of the on body electronics configured for operation with a two electrode analyte sensor in certain embodiments.

In certain embodiments, sensor 210 is inserted under the skin into the interstitial fluid of a user, and responds to changes in glucose concentration. The sensor 210 is a two terminal device including working electrode 211 and counter electrode 212 that can be electrically modeled as a current source which generates a current signal as a function of the detected or monitored glucose concentration. The sensor 210 output may be dependent on temperature. In certain embodiments, a high-value resistor is connected across the sensor terminals 211, 212 and may be part of the sensor assembly. In certain embodiments, sensor 210 is a self generating, self powered sensor and does not require a bias potential applied from an external power source. In certain embodiments, the sensor output may vary up to about 400 millivolts over the full range of glucose and temperature monitored and/or detected. Further detail of sensor 210 is provided in U.S. Patent Publication No. 2010/0213057 and U.S. Provisional Application No. 61/325,260, the disclosures of each of which are incorporated herein by reference.

Referring to FIG. 2, in certain embodiments, sensor 210 is operatively coupled to resistors 215a, 215b as shown whose terminals respectively are coupled to capacitors 216a, 216b. In certain embodiments, resistors 215a, 215b may include 2.5 MΩ resistors, while capacitors 216a, 216b may include 100 µFarad, 1 µFarad capacitors, respectively. Thermistor or other resistance temperature device (RTD) 282 and reference resistor 283 are provided as shown and coupled to ASIC 220.

In certain embodiments, upon initialization of sensor 210, reference resistance R is measured once and the measured resistance is stored (for example, in a memory device provided on ASIC 220). After measuring the reference resistance R, in certain embodiments, the resistance is measured or detected based on the measurement from the thermistor or RTD 282.

Referring to FIG. 2, in certain embodiments, ASIC 220 is powered by a magnetic field generated by the display device 120 (FIG. 1). As described above, the sensor interface in certain embodiments includes a network of two resistors 215a, 215b and two capacitors 216a, 216b across sensor electrodes 211, 212. In certain embodiments, ASIC 220 is configured to sample two voltages from this sensor network for each analyte measurement acquisition. In a steady-state, both differential voltages from the sensor network will be at similar in level and range from about 0 to 200 mV. Also shown in FIG. 2 is temperature detection circuit 280 coupled to 12 bit A/D converter 222 of ASIC 220 via analog multiplexer 221. The temperature detection circuit 280 includes current source 281, an external thermistor 282 and corresponding switch 284 and reference resistor 283 and corresponding switch 285. In certain embodiments, current source 281 includes one or more of a physical current source such as a resistor current source (e.g., a voltage source), an active current source (e.g., a transistor current source), or an inductor type current source (e.g., using a voltage regulator).

More specifically, in certain embodiments, ASIC 220 includes an internal band-gap temperature sensor 225 (e.g., having a forward voltage of a diode that is temperature dependent) with a predetermined level of or controlled slope variation (e.g., with a minimum tolerance threshold) from ASIC component to ASIC component during manufacturing, and the temperature sensor calibration may be achieved with a single point temperature calibration with, for example, a predetermined an offset error. Also shown in ASIC 220 are analog multiplexer 221 that interfaces with the sensor electrodes 211, 212, and is operatively coupled to 12-bit A.D converter 222, which in certain embodiments, may be controlled based at least in part on logic from state machine 223. In certain embodiments, ASIC 220 may include a processor, such as a reduced instruction set computing (RISC) processor or other processing unit containing programming to implement the logic of ASIC 220 in lieu of state machine 223.

In certain embodiments, to protect the integrity of the A/D conversion (such as, for example, to minimize undesirable noise affecting the A/D conversion), display device 120 (FIG. 1) may be configured to disable RF communication during the A/D conversion process. An external capacitor (not shown) of a few hundred nano Farads may be provided to store sufficient charge to power the A/D converter, based for example, upon logic implemented by state machine 223, in the absence of RF power from display device 120.

Referring still to FIG. 2, in certain embodiments, RF power is provided to the ASIC via the antenna 240 and RFID 224 and power 226 sections of the ASIC 220. When RF power is presented or within the range of antenna 240 and a predetermined RF command is received (for example, from display device 120), ASIC 220 may be configured to perform four A/D conversions—two conversions from the sensor 210 and two for the temperature measurement—and also, to store the raw A/D values in ASIC memory to be retrieved by display device 120. This routine in certain embodiments comprises one complete analyte measurement acquisition.

Figure 3:
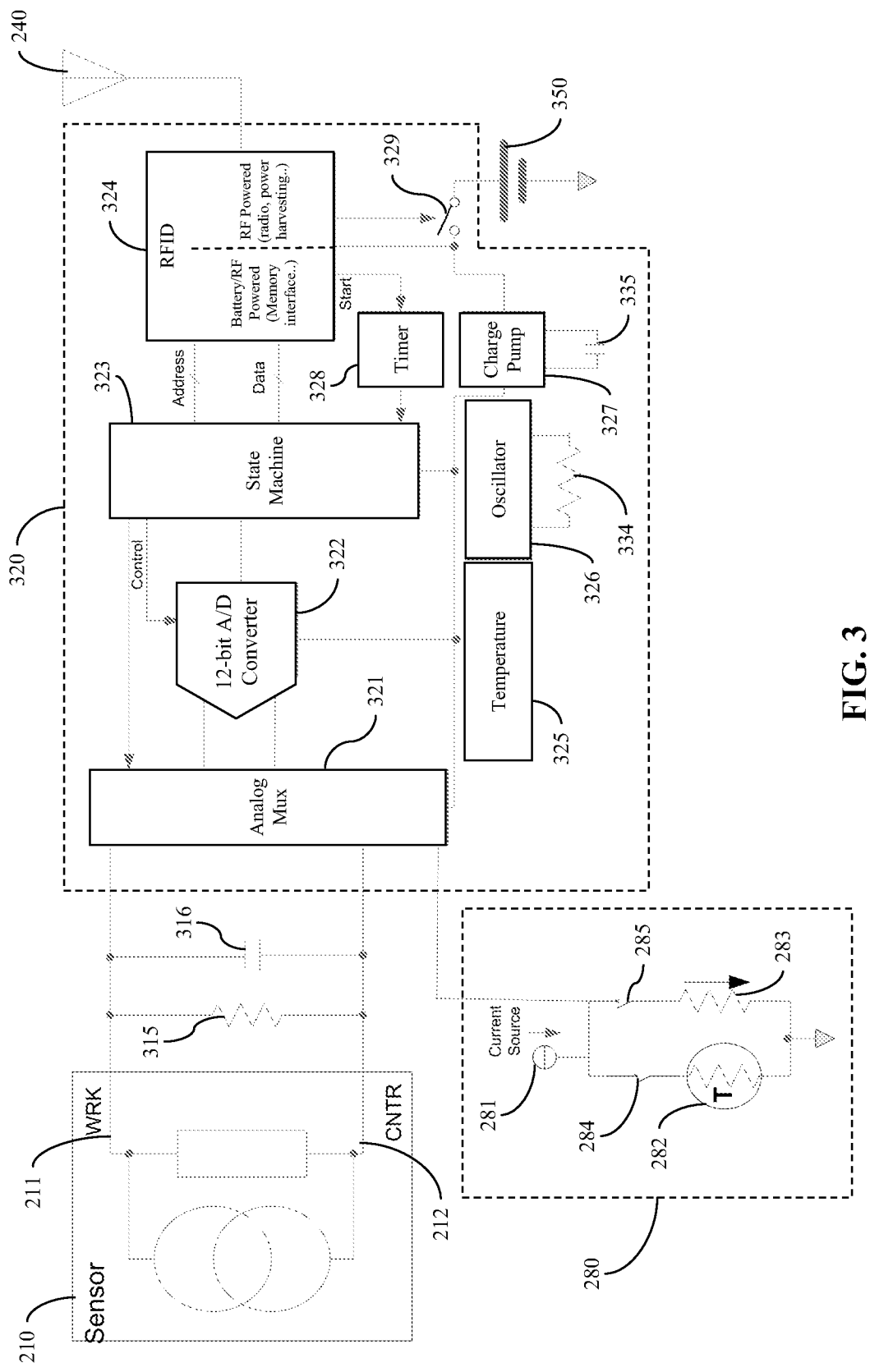
FIG. 3 illustrates a block diagram of the on body electronics configured for operation with a two electrode analyte sensor with a power source in certain embodiments.

FIG. 3 illustrates a block diagram of the on body electronics configured for operation with a two electrode analyte sensor with a power source in certain embodiments. Referring to FIG. 3, in the embodiment shown, battery 350 is provided with a switch 329 to allow for ASIC 320 to perform analyte level measurements with sensor 210 autonomously, and to be retrieved at a later time by display device 120 (FIG. 1). More specifically, the embodiment of ASIC 320 shown in FIG. 3 (compared to the embodiment shown in FIG. 2) includes charge pump 327 with capacitor 335 operatively coupled to the state machine 323, configured to convert the 1.5 Volts from battery 350 to about 3 Volts needed by ASIC 320 analog front-end circuitry for the measurement circuit. Also included in ASIC 320 is timer 328 which is a free-running timer clock providing a time of day information. In certain embodiments, a crystal oscillator 326 and resistor 334 may be provided.

Additionally, ASIC 320 may include extra memory for storage of measurement data, and battery isolation switch for long-term shelf life. Battery 350 may be configured to make analyte measurements without the RF power applied from display device 120 (FIG. 1). In this manner, only one differential voltage may need to be sampled between working electrode 211 and counter electrode 212 (coupled to resistor 315 (e.g., 5 MΩ) and capacitor 316 (e.g., 1 µFarad)) for each monitored analyte measurement.

In certain embodiments, analyte level trend information may be determined by display device 120 (FIG. 1) based on a pre-determined number of analyte measurements retained by ASIC 320. ASIC 320 in certain embodiments may measure each sample spaced at a pre-determined time interval and store each measurement in the ASIC memory. The oldest of the samples may be overwritten with each new sample taken. The retained data may be available to determine analyte level trend. Additionally, ASIC 320 may be configured to capture a pre-determined number of sensor and temperature samples spaced further apart for historical data logging for a total of about 8 hours. Within the scope of the present disclosure other suitable time periods may be used for historical data logging, such as 1 hour, 3 hours, 6 hours, 12 hours, 24 hours, 3 days, 5 days, 10 days, 14 days or more.

In certain embodiments, to provide sufficient time accuracy over an 8 hour period, for example (or other time periods), the internal clock of ASIC 320 may be configured to be as accurate to at least +/−3%. The accuracy may be improved or assisted by an external precision resistor.

Referring again to FIG. 3, battery isolation switch 329 may be configured to preserve the battery life during long-term inventory storage or increase the shelf life of battery 350. ASIC 320 in certain embodiments may be configured to activate battery isolation switch 329 upon receipt of a qualified or predetermined RF message or command from display device 120. Thus, the RFID portion 324 of the ASIC 320 may be configured to operate under RF power. Additional description of RF command or close proximity communication is provided in U.S. Pat. No. 7,826,382, the disclosure of which is incorporated herein by reference.

Further, as discussed above, internal band-gap temperature sensor 325 in certain embodiments includes a predetermined level of controlled slope variation (e.g., with a minimum tolerance threshold) from ASIC component to ASIC component during manufacturing, and the temperature sensor calibration may be achieved with a single point temperature calibration with, for example, a predetermined offset error. Provided below is a table illustrating exemplary, non limiting parameters and associated values for the embodiment shown in FIG. 3. While specific ranges and/or values are shown below, within the scope of the present disclosure, other ranges and/or values are contemplated.

| Item | Parameter | Value |
| --- | --- | --- |
| 1 | Charge pump input voltage range | 1.2 V to 1.8 V |
| 2 | External capacitance for charge pump | 2 uF max. |
| 3 | Battery switch off-mode leakage | 20 nA max. |
| 4 | Clock timer frequency accuracy (with external precision reference resistor) | +/−5%, from 5° C.-60° C. |
| 5 | Internal memory | 800 bytes, volatile or non-volatile |

Figure 4:
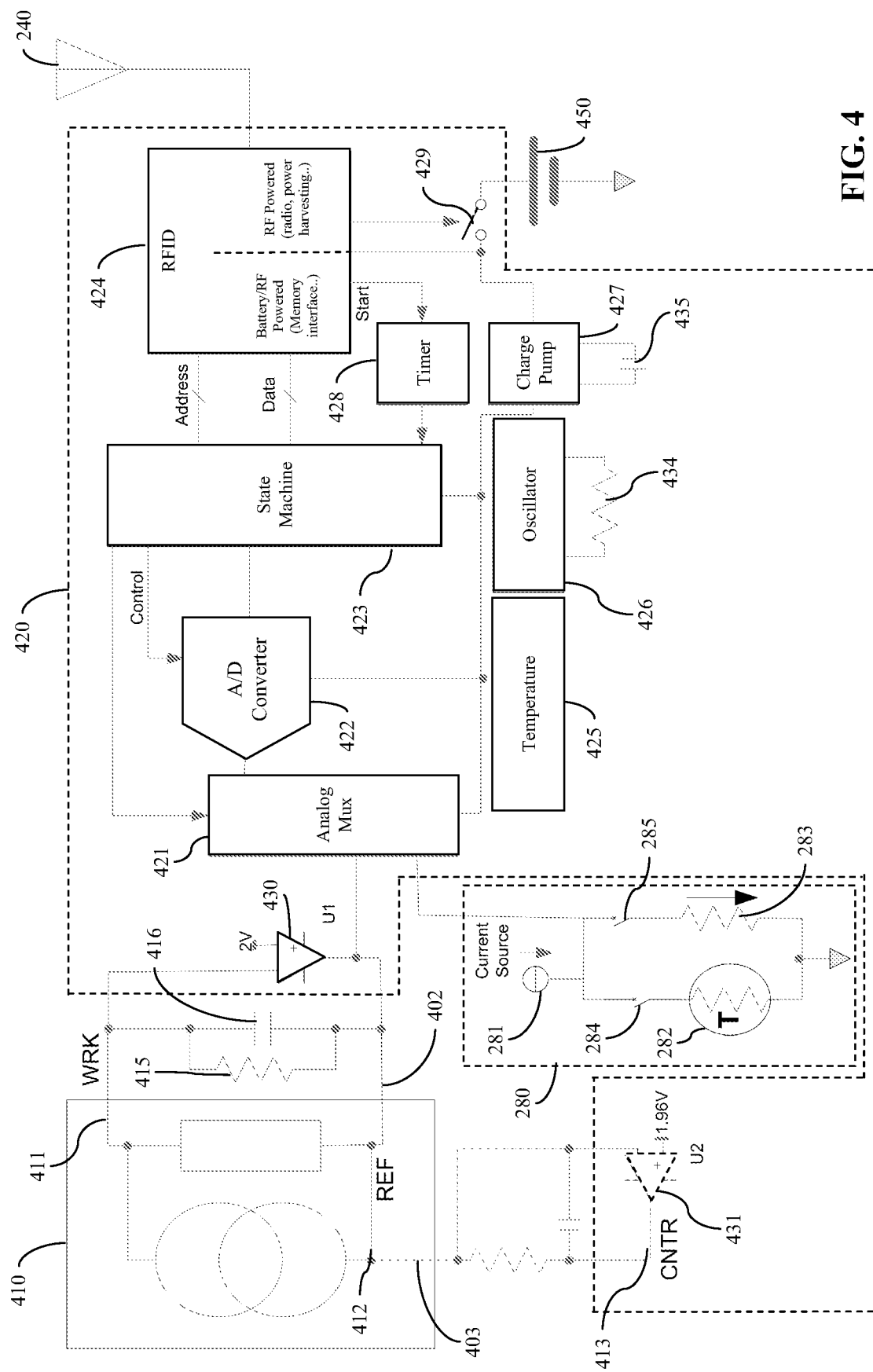
FIG. 4 illustrates a block diagram of the on body electronics configured for operation with a two electrode sensor or a three electrode analyte sensor in certain embodiments.

FIG. 4 illustrates a block diagram of the on body electronics configured for operation with a two electrode sensor or a three electrode analyte sensor in certain embodiments. Referring to FIG. 4, in certain embodiments, ASIC 420 may be configured for use with either a two electrode analyte sensor 410 or a three electrode analyte sensor. In certain embodiments, the two electrode sensor may include a working electrode (WRK) 411 and a reference electrode (REF) 412, while the three electrode sensor additionally includes a counter electrode (CNTR) 413. Referring still to FIG. 4, the sensor, whether a two electrode or a three electrode sensor, is coupled to ASIC 420 for operation.

In certain embodiments, the analog front end (AFE) of ASIC 420 includes two amplifiers, U1 430 and U2 431. As can be seen in FIG. 4, when a two electrode sensor is connected to the ASIC AFE, the inverting input terminal of amplifier U1 430 is coupled to the working electrode 411 of the sensor, the non-inverting input terminal of amplifier U1 430 is connected to a reference voltage source, and the output terminal of amplifier U1 430 is connected to the reference electrode 412, as illustrated by dotted line 402 of FIG. 4. In certain embodiments, a feedback resistor 415, which is a high resistance resistor (e.g., 5 MΩ resistor) and capacitor 416, are provided between the working and reference electrodes 411, 412 respectively. In certain embodiments where the sensor is a two electrode sensor, the connection between amplifier U2 431 and sensor 410 is open, such that amplifier U2 431 and the circuits shown with dotted line 403 are not connected to the sensor.

In certain embodiments where a three electrode sensor is connected to the ASIC AFE, the inverting input terminal of amplifier U1 430 is connected to the working electrode 411 of the sensor, just as in the two electrode sensor embodiments, however, the reference electrode 412 is coupled to the inverting input terminal of amplifier U2 431 instead of the output terminal of amplifier U1 430. Further, the counter electrode 413 may be coupled to the output terminal of amplifier U2 431. In the three electrode sensor embodiments, the connection between reference electrode 412 and amplifier U2 431 (dotted line 403) is closed thereby coupling amplifier U2 431 to sensor 410, while the connection between the output of amplifier U1 430 and the reference electrode 412 (dotted line 402) is open, such that the output of amplifier U1 430 is not connected to reference electrode 412 of the sensor.

Similar to the ASIC configuration of FIG. 3, in certain embodiments, ASIC 420 shown in FIG. 4 includes battery 450 provided with switch 429 such that ASIC 420 is configured to process and/or store analyte level measurements from sensor 410 autonomously. ASIC 420 as shown in FIG. 4 also includes charge pump 427 with capacitor 435 operatively coupled to state machine 423. Charge pump 427, in certain embodiments, is configured to convert the 1.5 Volt signal from battery 450 to about 3 Volts for ASIC 420 to operate to acquire, filter, store or otherwise process signals received from the analyte sensor 410. In certain embodiments, ASIC 420 also includes timer 428 which is a free-running timer clock providing a time of day information, crystal oscillator 426 and resistor 434 operatively coupled to crystal oscillator 426.

Referring back to FIGS. 3 and 4, also provided is temperature detection circuit 280 as shown and described in conjunction with FIG. 2 above, and which is coupled to the respective A/D converter 322 of ASIC 320 (FIG. 3), and to A/D converter 422 of ASIC 420 (FIG. 4) via the respective analog multiplexer 321, 421.

In certain embodiments, signals corresponding to monitored analyte levels from the sensor, whether a two electrode sensor or a three electrode sensor, are processed by ASIC 420. Referring to FIG. 4, in certain embodiments, ASIC 420 includes an A/D converter 422 which may be a 15 bit A/D converter. In certain embodiments, the A/D conversion may include a sigma-delta modulator. Sigma-delta modulation may provide other functions in addition to simple A/D conversion, including, but not limited to, adjustable conversion resolution, which may be proportional with the converter modulator clock frequency or acquisition period of the conversion, and signal filtering. Further, a sigma-delta modulator may be configured for low power consumption as a sigma-delta modulator may be configured for use with a low clock rate, utilizing less power. In certain embodiments, utilizing a longer duration acquisition period for the sigma-delta conversion may provide signal filtering of the data signals. Variation in the acquisition period duration may affect the level of signal filtering provided by the sigma-delta modulation.

In the manner described above, the ASIC power source may include a low-power disposable power source, e.g., a battery that may be used for the voltage source for the reference voltage signals for the amplifiers of ASIC 420 and to power the clock and sigma-delta modulator without draining the power source rapidly. In this manner, increased battery life may result and in turn, increased electronics use life can be attained. Further examples and details related to sigma-delta modulation and analog-to-digital conversion can be found in, among others, U.S. Patent Publication No. 2011/0060530, the disclosure of which is incorporated herein by reference for all purposes.

In certain embodiments, the configuration of ASIC 420 may be based on a 0 Volts to 2 Volts input voltage range of the A/D converter 422. In such embodiments, with an analyte sensor that requires a compliance range of about 2 Volts, a 2 Volt voltage source may be provided to the inverting terminal of amplifier U1 430, such that the terminal is biased at a fixed 2 Volts. This configuration may be applicable to both the two electrode and the three electrode analyte sensors. In the embodiments where the sensor is a three electrode analyte sensor, the input voltage to the positive terminal of amplifier U2 431 may be 1.96V. While specific values are provided for voltages, within the scope of the present disclosure, other voltages and ranges of voltages are contemplated.

For an analyte sensor current range of 0 nA to 85 nA and a feedback resistance of 5 MΩ, the output voltage of amplifier U1 430 may change by 0.425V (5,000,000Ω*85 nA), which in turn results in a A/D converter input voltage in the range of 2V-1.575V. In certain embodiments, ASIC clock, which may be provided by timer 428, includes a 32.786 KHz clock and the analyte measurement may be performed over a 30 second time window data acquisition period. In such embodiments, the resulting resolution of the A/D converter is approximately 30,720 counts full scale (approximately 15 bits), and the digital conversion of about 0 Volt to about 2 Volt input voltage range would be from 0 to 30,720 counts.

Referring still to FIG. 4, in certain embodiments, the transimpedance amplifier U1 430 may be used to convert sensor current into an output voltage. The range of sensor current that is accommodated include about 0 nA to about 85 nA. Moreover, in certain embodiments, A/D conversion range may include (0.425V/2V)*30,720=6,528 Counts. This provides a resolution of 13 pA. In certain embodiments, a low threshold for sensor sensitivity may be about 11.1 pA/mg/dL resulting in a resolution of about 1.1 mg/dL, for example.

The table below illustrates exemplary, non-limiting parameters and values for the embodiment shown in FIG. 4. As such, within the scope of the present disclosure, other ranges and/or values are contemplated:

| Item | Parameter | Value |
| --- | --- | --- |
| 1 | WRK electrode voltage | 2 V +/− 250 mV |
| 2 | Poise voltage = WRK − REF | 40 mV +/− 25 mV (part to part variation.) |
| 3 | Poise voltage stability (20° C. to 50° C.) | +/−25 mV. This means worse case stack up of part to part variation + temperature is 40 mV +/− 50 mV. |
| 4 | Servo Amplifier output voltage | 0.2 to WRK Potential (Volts) |
| 5 | Servo Amplifier input leakage current | <+/−10 pA (Biased at 1.96 V at about 25° C.) |

-continued

| Item | Parameter | Value |
|---|---|---|
| 6 | Servo Amplifier input offset Voltage | +/−10 mV |
| 7 | Servo Amplifier input offset drift | +/−75 uV/° C. |
| 8 | WRK Amplifier output voltage | 1.25 V to WRK Potential + 75 mV. |
| 9 | WRK Amplifier input leakage current | <+/−20 pA (Biased at about 2 Volts) |
| 10 | WRK Amplifier input offset Voltage | +/−10 mV |
| 11 | WRK Amplifier input offset drift | +/−75 uV/° C. |

In certain embodiments, one measurement cycle may include first 30 seconds including glucose data, second 15 seconds temperature thermistor or RTD data, third 15 seconds of internal temperature measurement to result in a total of 60 seconds per measurement cycle.

Table below provides exemplary, non limiting parameters and values for the analyte sensor analog front end electronics in certain embodiments. While specific values and/or ranges of values are shown below, within the scope of the present disclosure other suitable values or ranges of values are contemplated:

| Item | Parameter | Value |
|---|---|---|
| 1 | Sensor Measurement Resolution. The resolution covers the sensor sensitivity range, accomplishing 2 bits of this resolution with variable gain in front of the converter. | 12 bits or better for an input operating range of 425 mV. |
| 2 | Maximum input leakage current for both the condition where the ASIC is powered and also when it is not powered. (Assumes limited temperature range from (Specified 25° C. to 40° C.) and limited voltage input up to 100 mV) | <+/−10 pA (measured at 100 mV input at about 25° C.) |
| 3 | Total Measurement Error − Linearity post calibration error. (Assumes that offset is calibrated to +/−1 A/D Count and slope is calibrated to +/−0.5% at full scale.) | <+/−1.5% |
| 4 | AFE measurement. Thermal drift − change in offset post calibration. (Specified 25° C. to 40° C.) | +/−5 A/D Count. |
| 5 | AFE measurement. Thermal drift − slope (Specified 25° C. to 40° C.) | +/−1.5% |
| 6 | Electrostatic discharge (ESD) Protection | Achieve +/−2 KV human body model (HBM) for each pin on the ASIC. For low leakage inputs, use +/−500 V human body model (HBM). |
| 7 | RF interference | Measurement accuracy is maintained when the display device is used to acquire sensor data. Display device may terminate RF transmission temporarily for RF quieting during measurement. For the architectures with a battery, data may be marked "bad" if measurement occurs during RF communication. |

Figure 5:
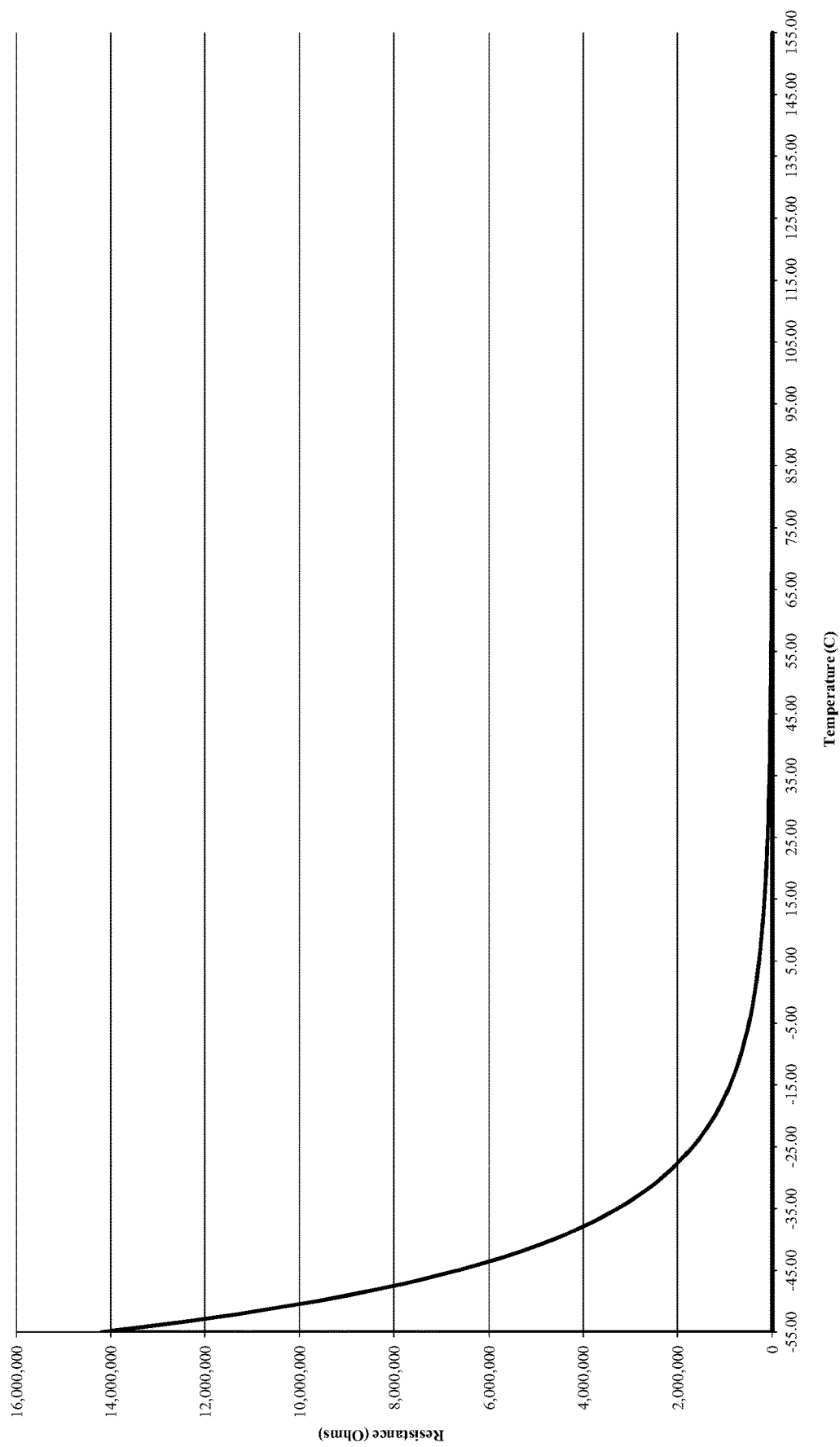
FIGS. 5 and 6 are graphical illustrations of thermistor characteristics for use in the analyte monitoring system of FIG. 1 in certain embodiments.
Figure 6:
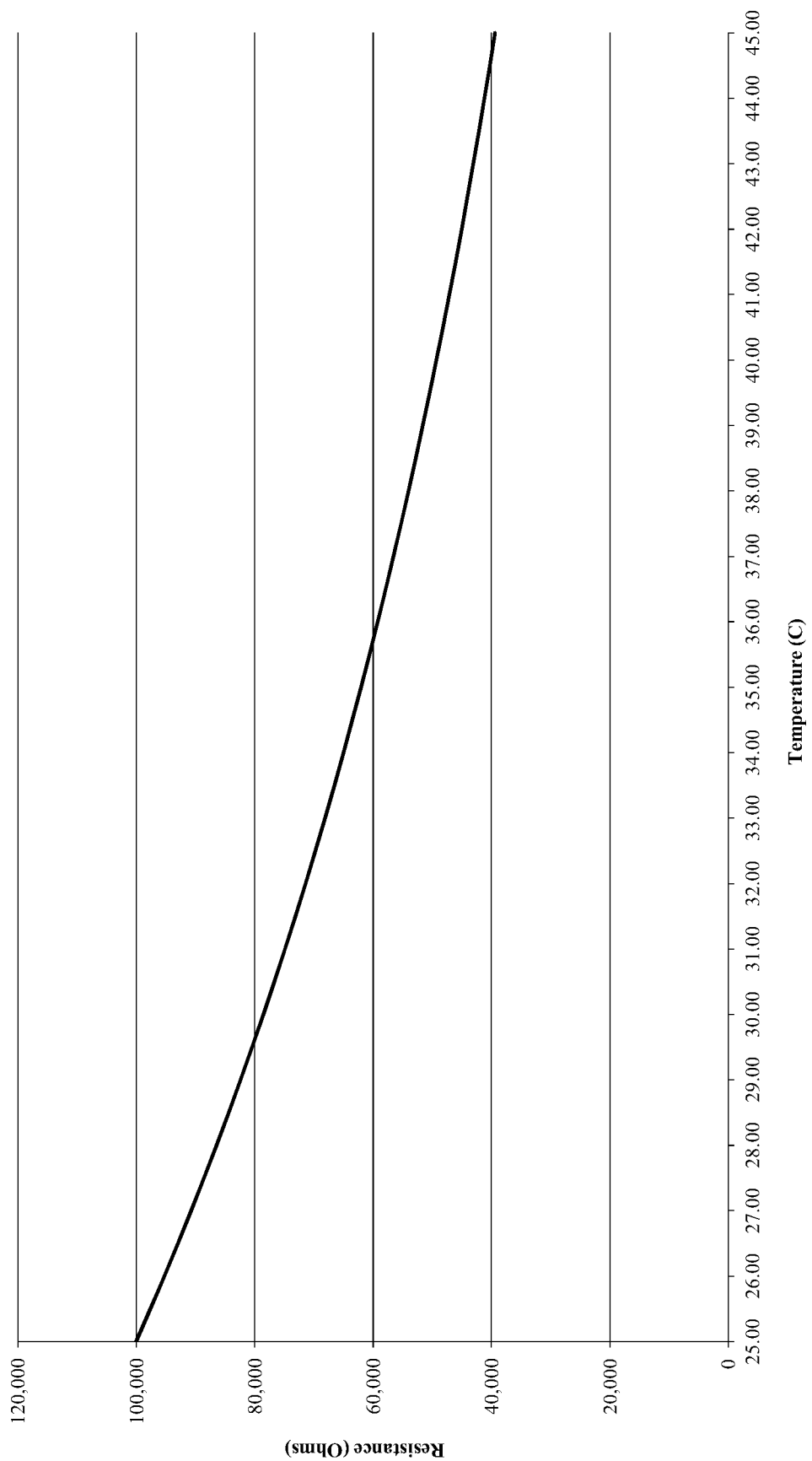

FIGS. 5 and 6 are graphical illustrations of thermistor characteristics for use in the analyte monitoring system of FIG. 1 in certain embodiments.

In certain embodiments, the ASIC may also be configured to accommodate two types of temperature sensors in addition to the two or three electrode analyte sensors. In certain embodiments, the temperature sensor is a resistive device, such as a thermistor or a resistive thermal device (RTD), in addition to a reference resistor. The resistive temperature sensor and the reference resistor are both ground referenced with a current source provided by the ASIC, in certain embodiments. In certain embodiments, the current source current is determined based on the desired input voltage range of the A/D converter. This current may be in the 1 pA or 1 mA range, for example. The input voltage range, and thus the current, may be based on the desired resolution of the output of the A/D converter. For example, utilizing a 32.768 KHz ASIC clock and a 15 second temperature detection acquisition window, operating at a 0 Volt to 0.5 Volt input range, the resulting resolution of the temperature sensor would be 0-3,840 counts, or 0.13 mV/count.

In certain embodiments, the sensor has about +7%/° C. dependency. Skin temperature may be measured using a thermistor 282. This method in certain embodiments, includes reference resistor 283 and the measurement thermistor 282 multiplexed into a 12 bit (or other suitable resolution) A/D converter. Excitation of the thermistor 282 and reference resistor 283 may utilize a common 1 µA current source 281.

In certain embodiments, an internal (e.g., internal to ASIC) temperature sensor 225 (FIG. 2), 325 (FIG. 3), 425 (FIG. 4) in addition to the external thermistor interface 280 may be provided. The internal temperature sensor 225, 325, 425 may be used for thermal gradient correction. As discussed above, internal ASIC temperature sensor may be calibrated using a single point temperature calibration. To this end, in certain embodiments, the part-to-part consistency of the slope of the temperature sensor in the ASIC component is maintained within a predetermined threshold range or above a preset level, and further, errors observed during temperature calibration may be attributed to offset errors.

In certain embodiments, the temperature sensor is a resistive device that can be either a thermistor or an RTD in addition to a reference resistor. The reference resistor and resistive temperature sensor are ground referenced and will have a current source excitation provided by the ASIC.

In certain embodiments, current source may be either in the 1 uA or 1 mA range depending on the device selected, and may be designed so that the desired input voltage range to the A/D is met. The input voltage range to the A/D converter in certain embodiments is sized to ensure that the desired resolution is achieved.

In certain embodiments, temperature and reference resistor measurement may be achieved over a 15 second acquisition period and the modulator clock may be 32,768 Hz/32=1,024 Hz and is derived from the ASIC 32.768 KHz clock. The resulting resolution over the operating input range 0V-0.5V may be 1,024*15*0.5/2=3840 counts or 0.13 mV/count. For a change from 40° C. to 41° C., the thermistor resistance changes by 49,304Ω to 47,124Ω. For an input range that accommodates down to 20° C.=0.5V the excitation current is given by: Excitation current=0.5V/128192=3.9 uA.

For this level of excitation, the change in A/D input at the worse case portion of the thermistor range (40° C.) is 49,304*3.9 uA-47,124*3.9 uA=8.5 mV. In certain embodiments, the effective thermistor temperature resolution includes 0.13/8.5=0.01° C.

In certain embodiments, the AFE for the temperature measurement interface may include the following characteristics and/or parameters. While specific values and/or ranges or values are provided below, within the scope of the present disclosure other suitable values and/or ranges of values are contemplated.

| Item | Parameter | Value |
|---|---|---|
| 1 | Resistive temperature sensor measurement resolution. | 12 bits over the input operating range. |
| 2 | Current source excitation. Compatible with A/D input requirement. | +/−12% |
| 3 | Channels | 1 100 KΩ at 25° C. Thermistor or 400 Ω RTD, and 1 Reference resistor for a total of 2 inputs. Individually multiplexed to the same A/D converter and the same current source. |
| 4 | Resistive temperature measurement. Thermal drift − offset. (specified 25° C. to 40° C.) | +/−10 A/D Count. |
| 5 | Resistive temperature measurement. Thermal drift − slope (specified 30° C. +/− 20° C.) | +/−0.5% |
| 6 | Internal band-gap temperature measurement resolution: | Less than or equal to about 0.3° C. |
| 7 | Internal band-gap temperature measurement offset error: | Less than or equal to about 10° C. |
| 8 | Internal band-gap temperature measurement slope variation part to part: | Less than or equal to about +/−1.5% |
| 6 | ESD Protection | It is desirable to achieve +/−2 KV HBM for each pin on the ASIC. |
| 7 | RF interference | The specifications for measurement accuracy must be met when the reader is being used to acquire data, or data must be marked "bad". |

In certain embodiments, ASIC architecture is configured to withstand a 10 MeV e-beam with a dosage of about 25 kGy to about 60 kGy, such as, about 35 kGy, about 40 kGy, about 45 kGy, about 50 kGy, about 55 kGy, for example, for the on body electronics sterilization process to attain a desired predetermined sterility assurance level (SAL) (e.g., approximately $10^{-6}$ SAL). In certain embodiments, one or more predetermined annealing profiles may be provided for radiation recovery. Additional description related to sterilization can be found in U.S. Patent Publication No. 2009/0257911, the disclosure of which is incorporated by reference.

Certain embodiments may include an analyte sensor including a plurality of electrodes, including an in vivo portion of the analyte sensor configured for fluid contact with a bodily fluid under a skin layer, the analyte sensor configured to monitor an analyte level in the bodily fluid and to generate one or more signals associated with the monitored analyte level, and sensor electronics including a sensor interface section and a data processing section, the sensor interface section configured to electrically couple to the plurality of electrodes of the analyte sensor, and the data processing section configured to process one or more signals received from the analyte sensor, wherein the sensor interface section includes an electrical interface to couple to two electrodes of the plurality of electrodes, or three electrodes of the plurality of electrodes, and further wherein the data processing section includes an application specific integrated circuit with programmable logic to perform one or more operations of the data processing section including processing the one or more signals from the analyte sensor for filtering, calibration, storage, transmission, or one or more combinations thereof.

In certain embodiments, the application specific integrated circuit may include a state machine, and wherein the state machine is configured to implement the programmable logic.

In certain embodiments, the application specific integrated circuit may include a reduced instruction set computing (RISC) processor, wherein the RISC processor includes programming configured to implement the programmable logic.

In certain embodiments, the generated one or more signals from the sensor may include voltage signals.

In certain embodiments, the generated one or more signals from the sensor may include current signals.

In certain embodiments, two electrodes of the plurality of electrodes may include an anode and a cathode, wherein the anode comprises carbon or gold and sensing chemistry, and further, wherein the cathode includes platinum or platinized carbon.

In certain embodiments, the three electrodes of the plurality of electrodes may include a working electrode, a counter electrode and a reference electrode, wherein the working electrode comprises one or more of carbon, gold, silver, or platinum.

Certain embodiments may further include an antenna operatively coupled to the sensor electronics and configured to communicate data associated with the monitored analyte level.

In certain embodiments, the antenna may include a radio frequency antenna.

In certain embodiments, the application specific integrated circuit may include a radio frequency identification (RFID) communication component operatively coupled to the antenna.

In certain embodiments, the RFID communication component may be configured to transmit data corresponding to the monitored analyte level to a remote location.

In certain embodiments, the RFID communication component may be configured to transmit the data in response to a request received from the remote location.

Certain embodiments may include providing an analyte sensor including a plurality of electrodes, including an in vivo portion of the analyte sensor for fluid contact with a bodily fluid under a skin layer, the analyte sensor for monitoring an analyte level in the bodily fluid and for generating one or more signals associated with the monitored analyte level, and providing sensor electronics including a sensor interface section and a data processing section, wherein providing sensor electronics includes configuring the sensor interface section to electrically couple to the plurality of electrodes of the analyte sensor, and configuring the data processing section to process one or more signals received from the analyte sensor, wherein configuring the sensor interface section includes providing an electrical interface to couple to two electrodes of the plurality of electrodes, or three electrodes of the plurality of electrodes, and further wherein configuring the data processing section includes providing an application specific integrated circuit with programmable logic to perform one or more operations of the data processing section including processing the one or more signals from the analyte sensor for filtering, calibration, storage, transmission, or one or more combinations thereof.

In certain embodiments, providing the application specific integrated circuit may include providing a state machine to implement the programmable logic to process the one or more signals.

In certain embodiments, providing the application specific integrated circuit may include providing a reduced instruction set computing (RISC) processor configured to implement the programmable logic to process the one or more signals.

In certain embodiments, the one or more signals generated by the analyte sensor may include voltage signals.

In certain embodiments, the one or more signals generated by the analyte sensor may include current signals.

Certain embodiments may further include operatively coupling an antenna to the sensor electronics.

Certain embodiments may further include transmitting data corresponding to the monitored analyte level to a remote location via a radio frequency identification (RFID) communication component of the application specific integrated circuit operatively coupled to the antenna.

In certain embodiments, transmitting data corresponding to the monitored analyte level may include transmitting the data in response to a request received from the remote location.

Various other modifications and alterations in the structure and method of operation of the embodiments of the present disclosure will be apparent to those skilled in the art without departing from the scope and spirit of the present disclosure. Although the present disclosure has been described in connection with certain embodiments, it should be understood that the present disclosure as claimed should not be unduly limited to such embodiments. It is intended that the following claims define the scope of the present disclosure and that structures and methods within the scope of these claims and their equivalents be covered thereby.

What is claimed is:

1. An analyte monitoring device, comprising:
   an analyte sensor comprising a working electrode and a reference electrode, the analyte sensor configured to monitor an analyte level in a bodily fluid in a body; and
   sensor electronics including a sensor interface section and a data processing section, wherein the sensor interface section is operatively coupled to the working electrode and the reference electrode of the analyte sensor and configured to apply a voltage differential between the working electrode and the reference electrode,
   wherein the data processing section is configured to process one or more signals received from the analyte sensor,
   wherein the data processing section includes a circuit with programmable logic to filter, calibrate, store or transmit the one or more signals received from the analyte sensor, and
   wherein a first circuit path extends between the working electrode and the reference electrode and traverses only one amplifier, wherein the working electrode is coupled to an input of the only one amplifier and the reference electrode is coupled to an output of the only one amplifier.

2. The device of claim 1, further including an antenna operatively coupled to the sensor electronics and configured to communicate data associated with the monitored analyte level.

3. The device of claim 2, wherein the circuit includes a radio frequency identification (RFID) communication component operatively coupled to the antenna.

4. The device of claim 1, wherein the data processing section comprises a multiplexer operatively coupled to the sensor interface section.

5. The device of claim 1, wherein the input to the only one amplifier is a first input, and a second input of the only one amplifier is coupled to a reference voltage supply node.

6. The device of claim 1, wherein the output of the only one amplifier feeds back to the input of the only one amplifier.

7. The device of claim 6, wherein the only one amplifier is in an application specific integrated circuit (ASIC), and the feedback path is not in the ASIC.

8. The device of claim 1, wherein the output of the only one amplifier feeds back to the input of the only one amplifier through a feedback resistor and a capacitor.

9. The device of claim 1, wherein the analyte sensor does not comprise a counter electrode.

10. The device of claim 1, wherein the first circuit path does not traverse a multiplexer.

11. The device of claim 1, wherein the only one amplifier is configured to receive a sensor current at the input and convert that sensor current to a voltage on the output.

12. A method of using an analyte monitoring device, wherein the analyte monitoring device comprises:
    an analyte sensor comprising a working electrode and a reference electrode, the analyte sensor configured to monitor an analyte level in a bodily fluid in a body; and
    sensor electronics including a sensor interface section and a data processing section, wherein the sensor interface section is operatively coupled to the working electrode and the reference electrode of the analyte sensor and configured to apply a voltage differential between the working electrode and the reference electrode,
    wherein a first circuit path extends between the working electrode and the reference electrode and traverses only one amplifier, wherein the working electrode is coupled to an input of the only one amplifier and the reference electrode is coupled to an output of the only one amplifier, the method comprising:
    communicating one or more signals from the analyte sensor to the data processing section; and
    processing, by a circuit of the data processing section, the one or more signals from the analyte sensor to filter, calibrate, store, or transmit the one or more signals.

13. The method of claim 12, wherein an antenna is operably coupled to the sensor electronics.

14. The method of claim 13, further comprising transmitting data corresponding to the monitored analyte level to a remote location via a radio frequency identification (RFID) communication component of the circuit operatively coupled to the antenna.

15. The method of claim 12, wherein the data processing section comprises a multiplexer operatively coupled to the sensor interface section.

16. The method of claim 12, wherein the input to the only one amplifier is a first input, and a second input of the only one amplifier is coupled to a reference voltage supply node.

17. The method of claim 12, wherein the output of the only one amplifier feeds back to the input of the only one amplifier.

18. The method of claim 17, wherein the only one amplifier is in an application specific integrated circuit (ASIC), and the feedback path is not in the ASIC.

19. The method of claim 12, wherein the output of the only one amplifier feeds back to the input of the only one amplifier through a feedback resistor and a capacitor.

20. The method of claim 12, wherein the analyte sensor does not comprise a counter electrode.

21. The method of claim 12, wherein the first circuit path does not traverse a multiplexer.

22. The method of claim 12, wherein the only one amplifier is configured to receive a sensor current at the input and convert that sensor current to a voltage on the output.

23. An analyte monitoring device, comprising:

an analyte sensor comprising a working electrode and a reference electrode, the analyte sensor configured to monitor an analyte level in a bodily fluid in a body; and sensor electronics including a sensor interface section and a data processing section, wherein the sensor interface section is operatively coupled to the working electrode and the reference electrode of the analyte sensor, wherein the data processing section is configured to process one or more signals received from the analyte sensor, wherein the data processing section includes a circuit with programmable logic to filter, calibrate, store or transmit the one or more signals received from the analyte sensor, and wherein a first circuit path extends between the working electrode and the reference electrode and traverses only one amplifier, wherein the working electrode is coupled to an input of the only one amplifier and the reference electrode is coupled to an output of the only one amplifier, and wherein the only one amplifier is configured to receive a sensor current at the input and convert that sensor current to a voltage on the output.

\* \* \* \* \*